(12) United States Patent
Sugita et al.

(10) Patent No.: US 7,674,262 B2
(45) Date of Patent: Mar. 9, 2010

(54) HIGH-FREQUENCY TREATMENT TOOL FOR ENDOSCOPE

(75) Inventors: Noriyuki Sugita, Saitama-ken (JP); Shinichi Matsuno, Kanagawa-ken (JP)

(73) Assignee: Hoya Corporation, Tokyo (JP)

( * ) Notice: Subject to any disclaimer, the term of this patent is extended or adjusted under 35 U.S.C. 154(b) by 703 days.

(21) Appl. No.: 11/349,090

(22) Filed: Feb. 8, 2006

(65) Prior Publication Data

US 2006/0178669 A1 Aug. 10, 2006

(30) Foreign Application Priority Data

Feb. 9, 2005 (JP) ............................. 2005-032391

(51) Int. Cl.
*A61B 18/14* (2006.01)

(52) U.S. Cl. .............................. 606/45; 606/41; 606/46

(58) Field of Classification Search .............. 606/32–47
See application file for complete search history.

(56) References Cited

U.S. PATENT DOCUMENTS

| | | | | |
|---|---|---|---|---|
| 3,906,955 | A | * | 9/1975 | Roberts ........................ 606/49 |
| 4,043,342 | A | * | 8/1977 | Morrison, Jr. ................. 606/48 |
| 4,708,137 | A | * | 11/1987 | Tsukagoshi ................... 606/46 |
| 5,281,218 | A | * | 1/1994 | Imran .......................... 606/41 |
| 5,626,577 | A | * | 5/1997 | Harris .......................... 606/41 |
| 5,817,067 | A | * | 10/1998 | Tsukada ...................... 604/256 |
| 6,083,202 | A | * | 7/2000 | Smith ..................... 604/164.01 |
| 6,093,195 | A | | 7/2000 | Ouchi |
| 6,210,398 | B1 | | 4/2001 | Ouchi |
| 6,258,064 | B1 | * | 7/2001 | Smith et al. ............. 604/164.12 |
| 6,423,060 | B1 | | 7/2002 | Ouchi |
| 6,743,206 | B1 | * | 6/2004 | Smith et al. ............. 604/164.01 |
| 2004/0210284 | A1 | | 10/2004 | Okada |
| 2005/0080411 | A1 | | 4/2005 | Ouchi |
| 2005/0215996 | A1 | | 9/2005 | Ouchi |

FOREIGN PATENT DOCUMENTS

| | | |
|---|---|---|
| JP | 10-165359 | 6/1986 |
| JP | 3244660 | 10/2001 |
| JP | 2002-113016 | 4/2002 |
| JP | 2004-313537 | 11/2004 |

OTHER PUBLICATIONS

U.S. Appl. No. 11/326,411 to Sugita et al., filed Jan. 6, 2006.
U.S. Appl. No. 11/349,083 to Sugita et al., filed Feb. 8, 2006.
U.S. Appl. No. 11/349,084 to Sugita et al., filed Feb. 8, 2006.

* cited by examiner

*Primary Examiner*—Michael Peffley
*Assistant Examiner*—Ronald Hupczey, Jr.
(74) *Attorney, Agent, or Firm*—Greenblum & Bernstein P.L.C.

(57) ABSTRACT

A high-frequency treatment tool for an endoscope including a flexible sheath being made of electrically insulating material to be inserted through an insertion channel of the endoscope, a conductive operation wire, which is adapted to be advanced and retracted inside the flexible sheath, and a partially elongated electrode being arranged at a distal end of the high-frequency treatment tool separately from the operation wire, to which high-frequency electrical current is supplied for high-frequency treatment, is provided. The electrode is adapted to be protruded and retracted in an axial direction thereof from the distal end of the high-frequency treatment tool by an operation to the operation wire. The electrode is allowed to be removed from the high-frequency treatment tool independently from the operation wire.

14 Claims, 9 Drawing Sheets

HIGH-FREQUENCY TREATMENT TOOL FOR ENDOSCOPE

BACKGROUND OF THE INVENTION

The present invention relates to a high-frequency treatment tool for an endoscope.

Generally, in a high-frequency treatment tool that is inserted through an instrument channel of an endoscope and is used for incision of mucous membranes of in vivo tissues inside a body cavity, a partially elongated electrode is equipped at a distal portion of an insulated flexible sheath. The electrode is connected to a conductive operation wire, which can be operated from a proximal side thereof so that the electrode can be protruded outwardly or retracted inwardly from the distal end of the sheath. The high-frequency treatment tool is widely used and examples of such a tool are disclosed in Japanese Patent Provisional Publication No. P2002-113016A and US Patent Application Publication No. US 2004/0210284 A1.

When the high-frequency treatment tool is used for the incision, an electrical current with high-frequency flows at a portion where the electrode contact the mucous membranes, and surface of the in vivo tissues is cauterized, thereby the incision is performed. Once the high-frequency treatment as above is performed, the surface of the electrode is oxidized, and thereafter, the living tissues easily stick to the electrode surface and are charred. In such a state, the conductivity of the high-frequency electrode is significantly deteriorated, therefore the electrode is required to be replaced. When cleaning of such an electrode is attempted by scraping, the electrode may be damaged, therefore the electrode may still need to be replaced.

Conventional electrodes, however, as seen in the above referenced publications, are fixed to the operation wires. Therefore, when the electrodes are replaced, operation wires as well or entire units including the flexible sheaths must be replaced, which is wasteful and uneconomical.

SUMMARY OF THE INVENTION

The present invention is advantageous in that a high-frequency treatment tool for an endoscope with an exchangeable electrode is provided. With the exchangeable electrode that can be replaced independently from the flexible sheath, the high-frequency treatment tool can be economically maintained in a clean condition.

According to an aspect of the present invention, a high-frequency treatment tool for an endoscope including a flexible sheath being made of electrically insulating material to be inserted through an insertion channel of the endoscope, a conductive operation wire, which is adapted to be advanced and retracted inside the flexible sheath, and a partially elongated electrode being arranged at a distal end of the high-frequency treatment tool separately from the operation wire, to which high-frequency electrical current is supplied for high-frequency treatment, is provided. The electrode is adapted to be protruded and retracted in an axial direction thereof from the distal end of the high-frequency treatment tool by an operation to the operation wire. The electrode is allowed to be removed from the high-frequency treatment tool independently from the operation wire.

Optionally, the electrode may be adapted to be advanced toward a distal end thereof by the operation wire.

Optionally, the high-frequency treatment tool may include a spring to provide expanding force toward a proximal end of the electrode to the electrode.

Optionally, the high-frequency treatment tool may include an operation unit, which is provided at a proximal end of the flexible sheath and is adapted to advance and retract the operation wire, and a fixing member, which is provided to the operation unit to fix the operation wire in an arbitrary position with an arbitrary length of the electrode being protruded from the distal end of the high-frequency treatment tool by the expanding force of the spring.

Optionally, the high-frequency treatment tool may include a capping member, which is detachably attached to the distal end of the flexible sheath. The capping member may have an opening in which the electrode is adapted to traverse. The electrode may be allowed to be removed from the high-frequency treatment tool when the capping member is removed from the distal end of the flexible sheath.

Optionally, the capping member may be adapted to be screwed to the distal end of the flexible sheath.

Optionally, the capping member may be adapted to be attached to the distal end of the flexible sheath with magnetic intensity.

Optionally, the electrode may include a rod portion, which is formed to traverse inside the opening to be protruded from the capping member, and a base portion, which is formed to loosely fit into an inner surface of the capping member. The spring may be arranged compressedly inside the capping member.

Optionally, the operation wire may be adapted to be in contact with a proximal surface of the base portion of the electrode.

Optionally, a distal end of the operation wire may include a bent portion, which is formed to be bent sidewardly with respect to an axial direction of the operation wire. The bent portion may be adapted to be in contact with the proximal surface of the base portion of the electrode.

Optionally, the sheath may be therein provided with a water channel, which is arranged in parallel with the operation wire. The base portion of the electrode and the capping member may be respectively provided with a water hole, which is in an approximate straight alignment with respect to the water channel.

Optionally, the base portion of the electrode may be provided with a locking system that is adapted to restrict the electrode from being rotated circumferentially with respect to the sheath.

According to an aspect of the present invention, an electrode for high-frequency treatment tool that is arranged separately from a conductive operation wire of the high-frequency treatment tool at a distal end of the high-frequency treatment tool is provided. The electrode includes a rod portion, which is formed to traverse inside an opening of a capping member of the high-frequency treatment tool to be protruded from the capping member, and a base portion, which is formed to loosely fit into an inner surface of the capping member. High-frequency electrical current is supplied for high-frequency treatment to the electrode. The electrode is adapted to be protruded and retracted in an axial direction thereof from the distal end of the high-frequency treatment tool by an operation to the operation wire. The electrode is allowed to be removed from the high-frequency treatment tool independently from the operation wire.

According to an aspect of the present invention, an endoscope with a high-frequency treatment tool for high-frequency treatment is provided. The high-frequency treatment tool includes a flexible sheath being made of electrically insulating material to be inserted through an insertion channel of the endoscope, a conductive operation wire, which is adapted to be advanced and retracted inside the flexible sheath, and a partially elongated electrode being arranged at a distal end of the high-frequency treatment tool separately from the operation wire to which high-frequency electrical current is supplied for high-frequency treatment. The electrode is adapted to be protruded and retracted in an axial direction thereof from the distal end of the high-frequency treatment tool by an operation to the operation wire. The electrode is allowed to be removed from the high-frequency treatment tool independently from the operation wire.

DETAILED DESCRIPTION OF THE EMBODIMENTS

Hereinafter, referring to the accompanying drawings, a high-frequency treatment tool according to illustrative embodiments of the invention will be described.

First Embodiment

Figure 1:
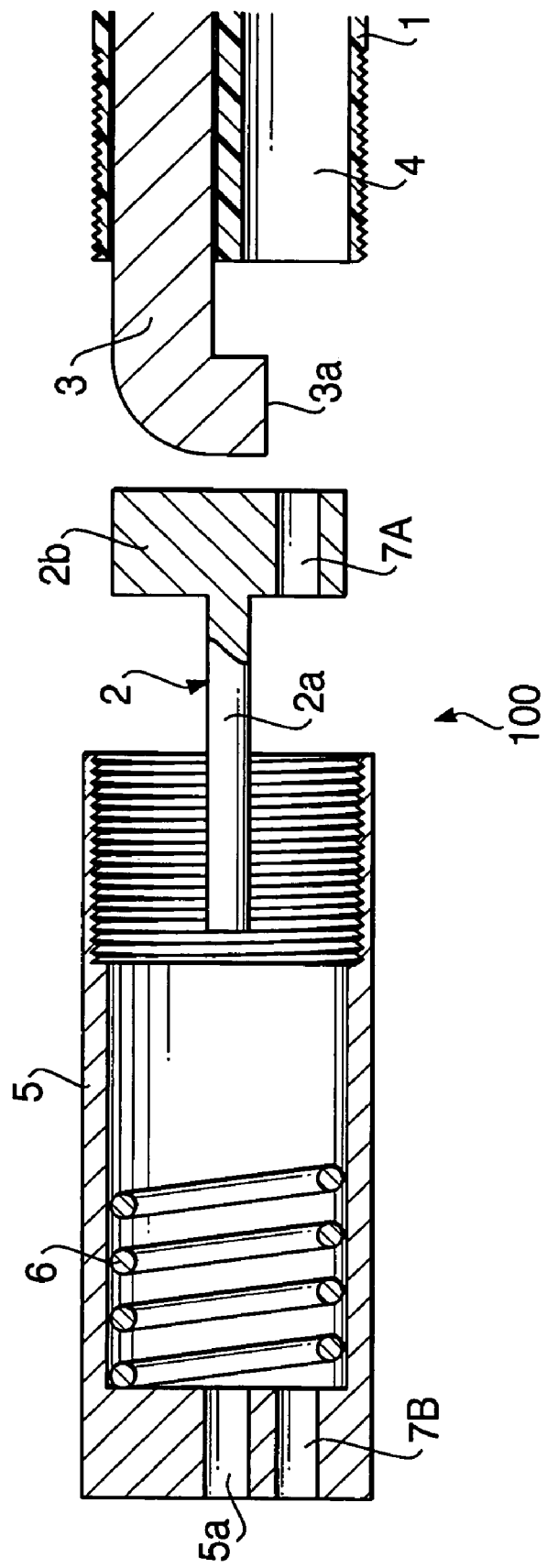
FIG. 1 is a cross-sectional side view of an exploded tip portion of a high-frequency treatment tool according to a first embodiment of the invention.
Figure 2:
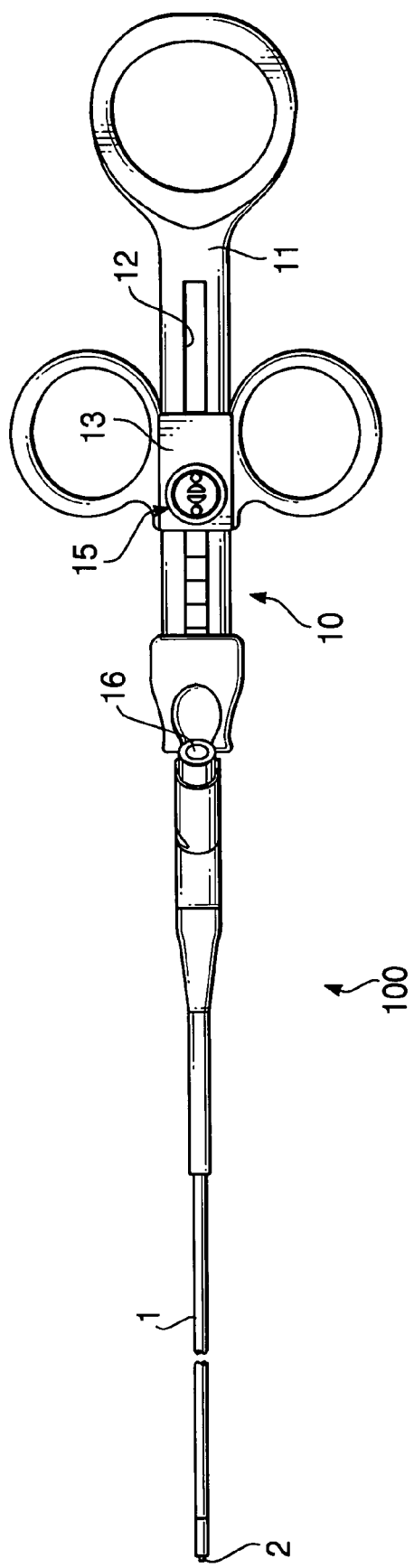
FIG. 2 shows a plane view of an entire configuration of the high-frequency treatment tool according to the first embodiment of the invention.
Figure 3:
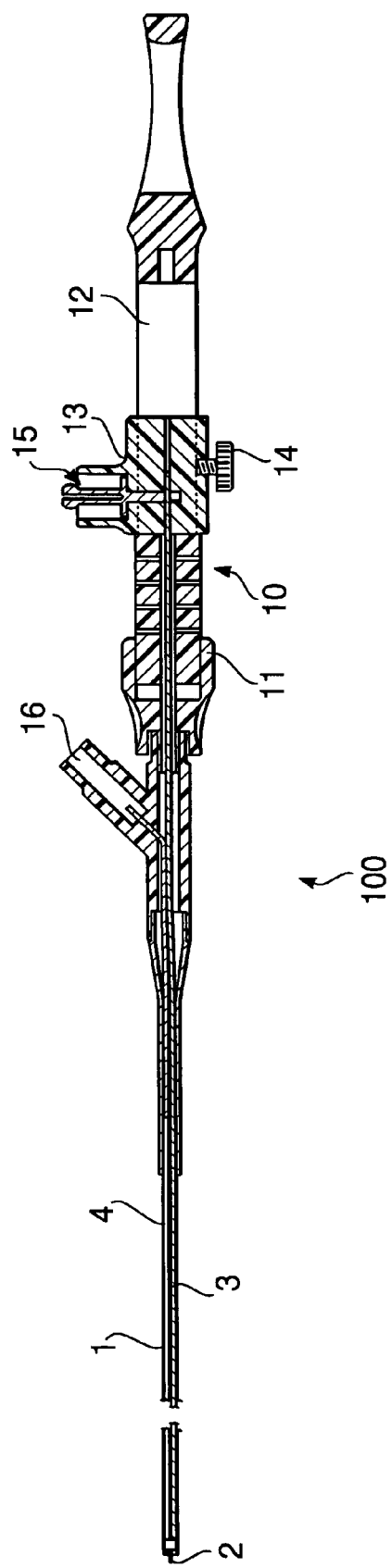
FIG. 3 shows a cross-sectional side view of the entire configuration of the high-frequency treatment tool according to the first embodiment of the invention.

FIG. 1 is a cross-sectional side view of an exploded tip portion of a high-frequency treatment tool 100 according to a first embodiment of the invention. FIG. 2 shows a plane view of an entire configuration of the high-frequency treatment tool 100 according to the first embodiment of the invention. FIG. 3 shows a cross-sectional side view of the entire configuration of the high-frequency treatment tool 100 according to the first embodiment of the invention.

The high-frequency treatment tool 100 includes a flexible sheath 1, a partially elongated electrode 2, and a conductive operation wire 3. The sheath 1 is inserted through an instrument channel (not shown) and formed with an insulated material, for example polytetrafluoroethylene. The electrode 2 is arranged at a distal portion of the sheath 1, and is configured to be protruded outwardly and retracted inwardly by an operation from a user via the operation wire 3, which can be advanced and retracted inside the sheath 1.

The sheath 1 is formed to be a multi-lumen tube, which includes a plurality of (for example, two) independent lumens formed in parallel with each other through the entire length of the sheath 1. The operation wire 3 is inserted through one lumen 1a of the two lumens, and the other lumen is used as a water channel 4.

The high-frequency treatment tool 100 is equipped with an operation unit 10, which is provided at a proximal end of the sheath 1. The operation unit 10 includes an operation shaft 11, which is connected to the proximal end of the sheath 1, a slit 12, which is formed in an axial direction of the operation shaft 11, and a slidable portion 13, which is adapted to slide along the slit 12. The slidable portion 13 is connected to a proximal end of the operation wire 3, which is advanced and retracted in the axial direction of the operation shaft 11 inside the sheath 11 with the slidable portion 13 being slid in the axial direction by the user.

The slidable portion 13 is provided with a manual setscrew 14, which is adapted to manually fix the slidable portion 13 with respect to the operation shaft 11 in an arbitrary position by being screwed by the user.

The slidable portion 13 is further provided with a terminal 15, to which a power supplying cable (not shown) is connected, so that electrical current with high-frequency can be supplied to the operation wire 3.

The high-frequency treatment tool 100 is further provided with a water filler port 16, which is in communication with the water channel 4.

Figure 4:
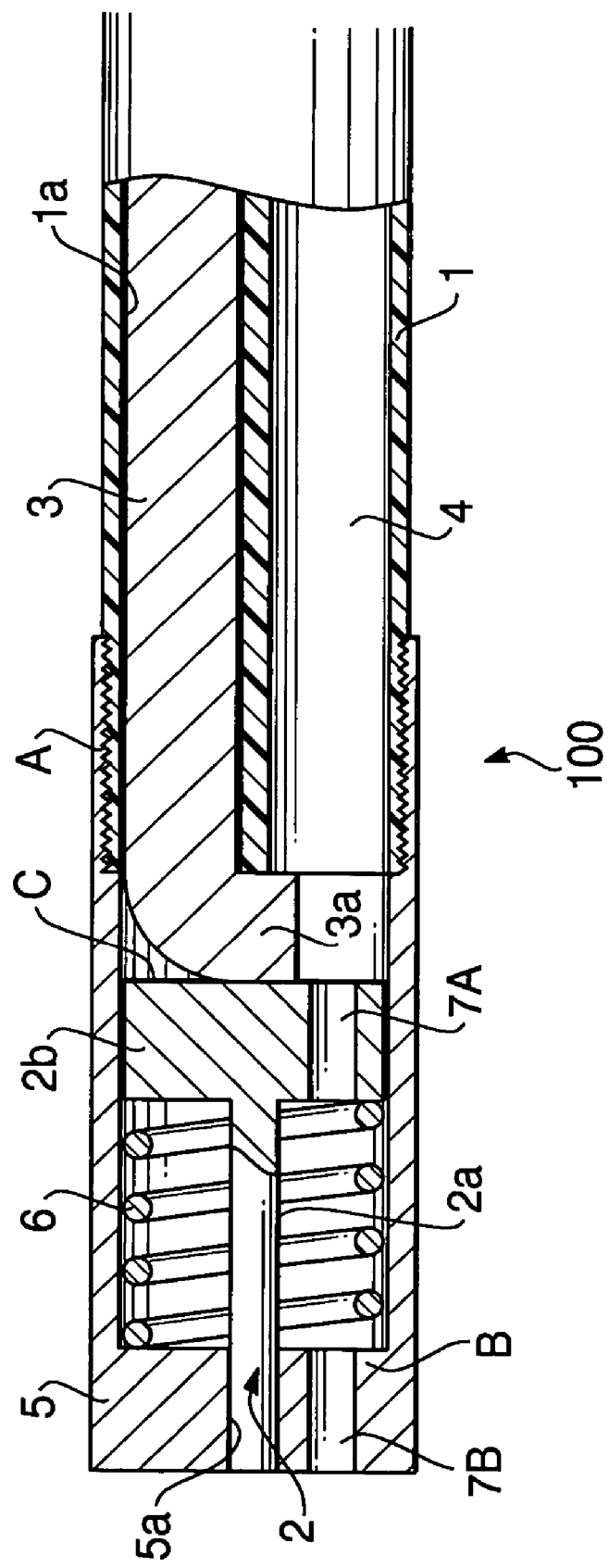
FIG. 4 shows a cross-sectional side view of the tip portion of the high-frequency treatment tool with an electrode retracted inwardly according to the first embodiment of the invention.

FIG. 4 shows a cross-sectional side view of a tip portion of the high-frequency treatment tool 100 with the electrode 2 retracted inwardly according to the first embodiment of the invention. The electrode 2, made of conductive metal, is arranged inside a capping member 5, which is detachably attached to the distal end of the sheath 1. The electrode 2 is unfixed to the operation wire 3, and is adapted to slide in the axial direction of the capping member 5.

In the present embodiment, the capping member 5 is screwed to the distal end of the sheath 1 at portion A. The capping member 5 is adapted to be detached from the sheath 1 by being rotated in a circumferential direction thereof and thus by being unscrewed.

The electrode 2 is integrally formed with a rod 2a, which is elongated in the axial direction of the high-frequency treatment tool 100, and a base 2b at a proximal end thereof. The rod 2a is traversable inside a hole 5a, which is formed in a center of the distal portion of the capping member 5, however, the base 2b is not allowed to proceed into the hole 5a. The base 2b is configured to loosely fit into an inner surface of the capping member 5, so that the electrode 2 can traverse inside the capping member 5.

Inside the capping member 5, a coiled spring 6 is arranged compressedly between a distal inner surface B and the base 2b. With expanding force of the coiled spring 6, the electrode 2 is steadily pressed toward the proximal end of the capping member 5, and a rear surface C of the base 2b is pressed to be in contact with a distal end 3a of the operation wire 3.

It should be noted that in the present embodiment the distal end 3a of the operation wire 3 is bent approximately perpendicularly at a position where the operation wire 3 is protruded toward the distal end of the capping member 5, so that the bent portion is in contact with the base 2b of the electrode 2.

The distal end 3a may be soldered to maintain the bent state. It should be also noted that the distal end 3a may be left simply to maintain a cutting plane. Also, the distal end 3a may be equipped with a metal tip that is suitable to have the electrode 2 to be in connection with the operation wire 3.

A water hole 7A, penetrating through the base 2b of the electrode 2, and a water hole 7B, penetrating through a distal wall 5d of the capping member 5, are provided in an approximate straight alignment with respect to the water channel 4 so that water advanced through the water channel 4 is further advanced and ejected forwardly from the capping member 5.

With the above-described configuration, the high-frequency treatment tool 100 is adapted to have the electrode 2 retracted in the capping member 5 with the expanding force of the coiled spring 6 toward the proximal end of the capping member 5 in an ordinary state, as shown in FIG. 4.

Figure 5:
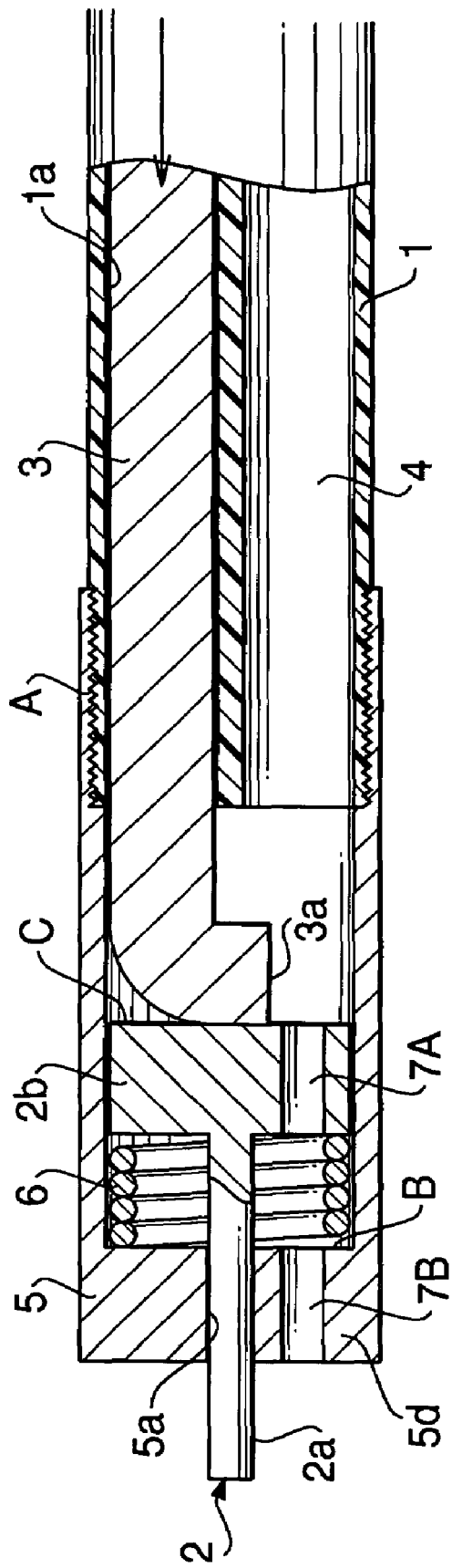
FIG. 5 shows a cross-sectional side view of the tip portion of the high-frequency treatment tool with the electrode protruded outwardly according to the first embodiment of the invention.
Figure 6:
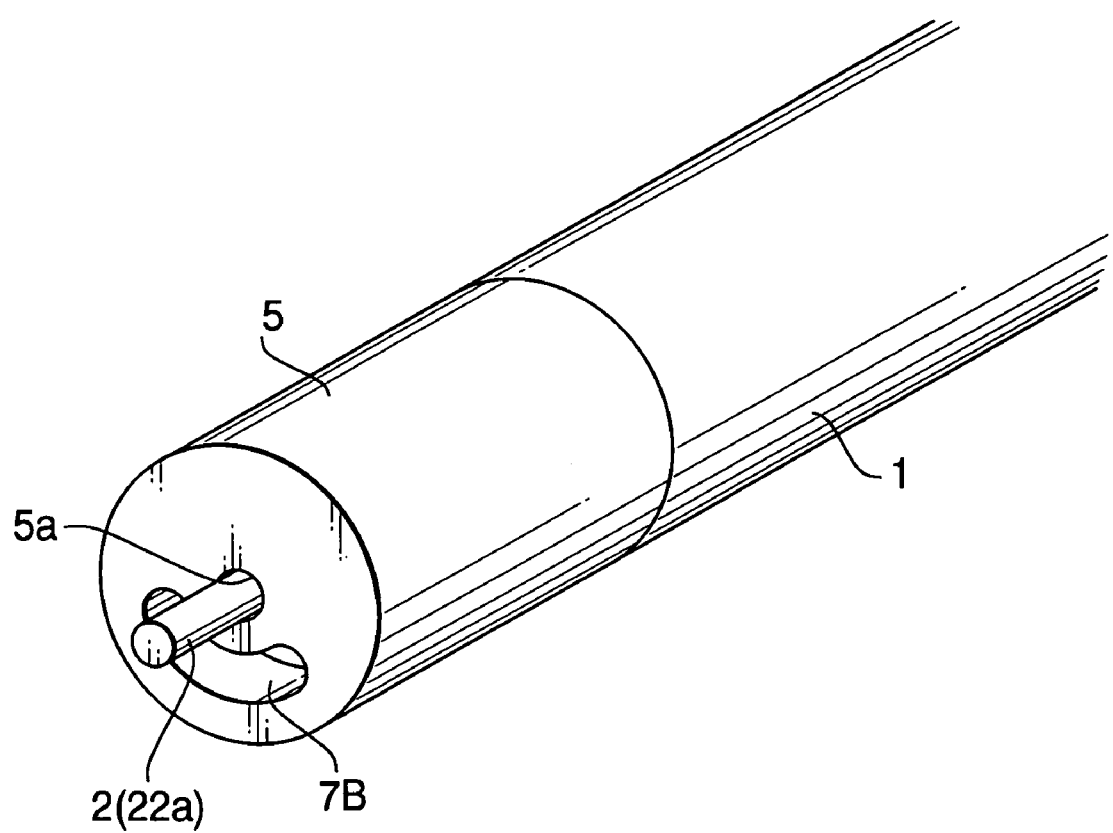
FIG. 6 shows a perspective view of the tip portion of the high-frequency treatment tool with the electrode protruded outwardly according to the first embodiment of the invention.

When the user operates the operation wire 3 by pressing the operation handle 10 toward the distal end of the high-frequency treatment tool 100, the electrode 2 is forwarded via the operation wire 3, as shown in FIGS. 5 and 6, against the expanding force of the coiled spring 6. Then, rod 2a of the electrode 2 is slid to be protruded outwardly from the capping member 5.

When the user retracts the operation wire 3 even slightly by pulling the operation handle 10, the rod 2a of the electrode 2 is retracted in the capping member 5 by the expanding force of the coiled spring, and the electrode 2 and the operation wire 3 remain contacted. With this state, the user can tighten the manual setscrew 14 (fixing member) to fix the operation wire 3 in an arbitrary position with an arbitrary length of the rod 2a being protruded.

Further, when the electrode 2 is replaced, in case for example cauterized living tissues stick to the rod 2a, only the electrode 2 can be taken out from the high-frequency treatment tool 100 by removing the capping member 5 from the distal end of the sheath 1, as shown in FIG. 1, and the other components including the operation wire 3 can be maintained to be used further.

Second Embodiment

Figure 7:
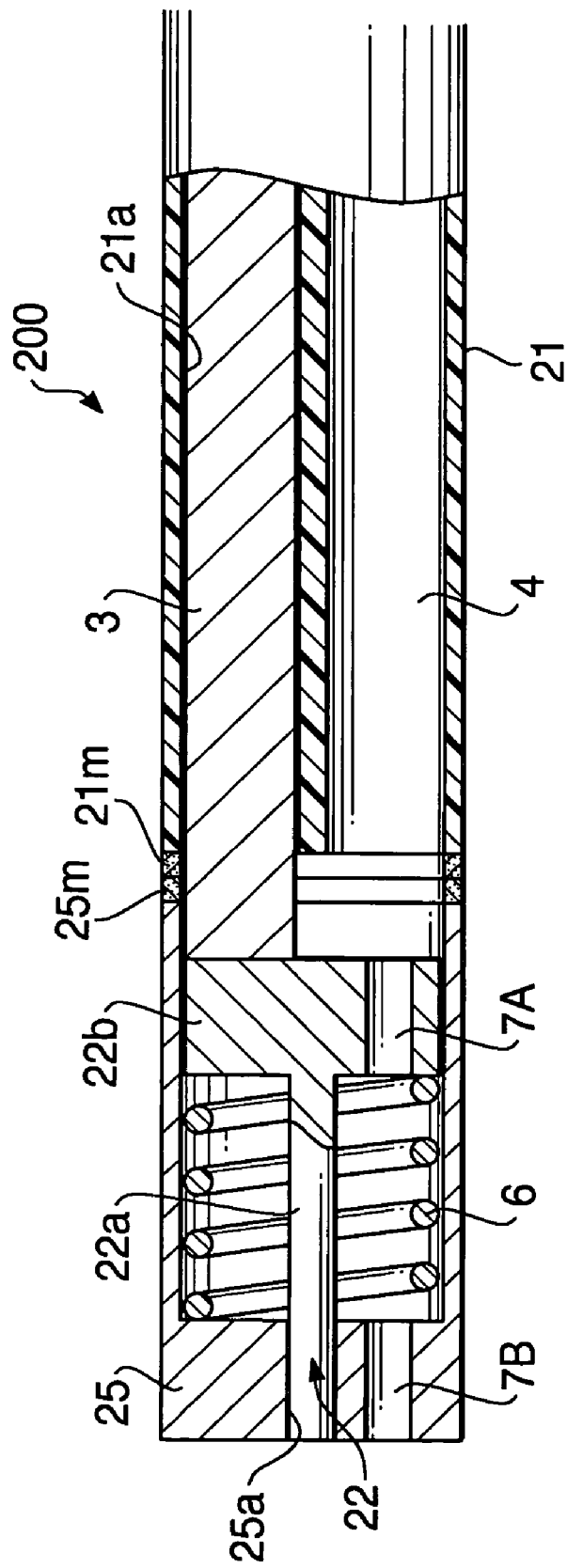
FIG. 7 shows a cross-sectional side view of a tip portion of a high-frequency treatment tool according to a second embodiment of the invention.

FIG. 7 shows a cross-sectional side view of a tip portion of a high-frequency treatment tool 200 according to a second embodiment of the invention. In the present embodiment, a capping member 25 is detachably attached to a sheath 21 with magnetic intensity. The sheath 21 is provided with a magnetic member 21m at a distal end thereof, and the capping member 5 is provided with a magnetic member 25m at a proximal end thereof, so that the two magnetic members 21m, 25m are attracted to each other.

Figure 8:
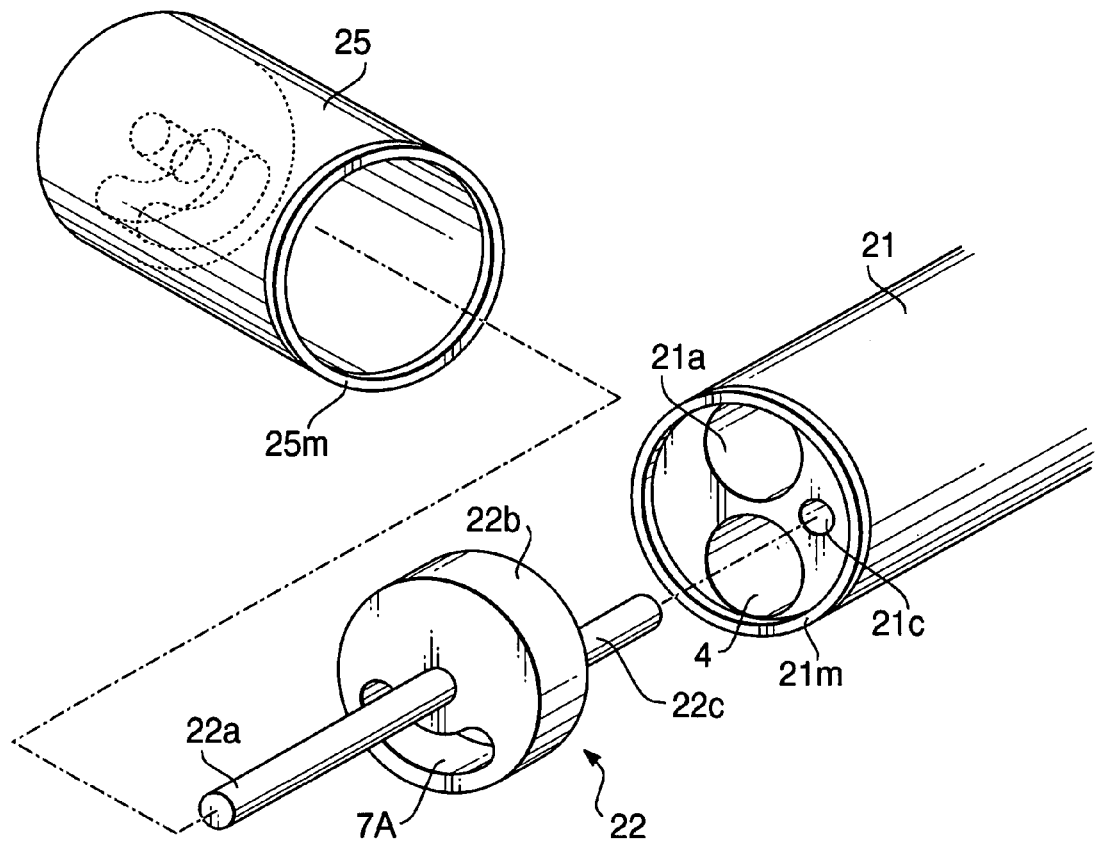
FIG. 8 is an exploded view of the tip portion of the high-frequency treatment tool according to the second embodiment of the invention.

FIG. 8 is an exploded view of the tip portion of the high-frequency treatment tool 200 according to the second embodiment of the invention. FIG. 8 shows a state of the tip portion wherein the capping member 25 is removed from the distal end of the sheath 21 and the electrode 22 is taken out. An electrode 22 is integrally formed with a guide pin 22c that protrudes toward a proximal end of the sheath 21. The guide pin 22c is in a straight alignment with respect to a rod 22a. The sheath 21 is provided with a guide hole 21c, into which the guide pin is loosely fit, at a distal portion thereof, so that the electrode 22 is restricted from rotating in a circumferential direction thereof inside the capping member 25. As in the first embodiment, the rod 22a is traversable inside a hole 25a, wich is formed in a center of a distal portion of the capping member 25. The sheath 21 includes a lumen 21a for operation wire 3, and another lumen used as a water channel 4.

Figure 9:
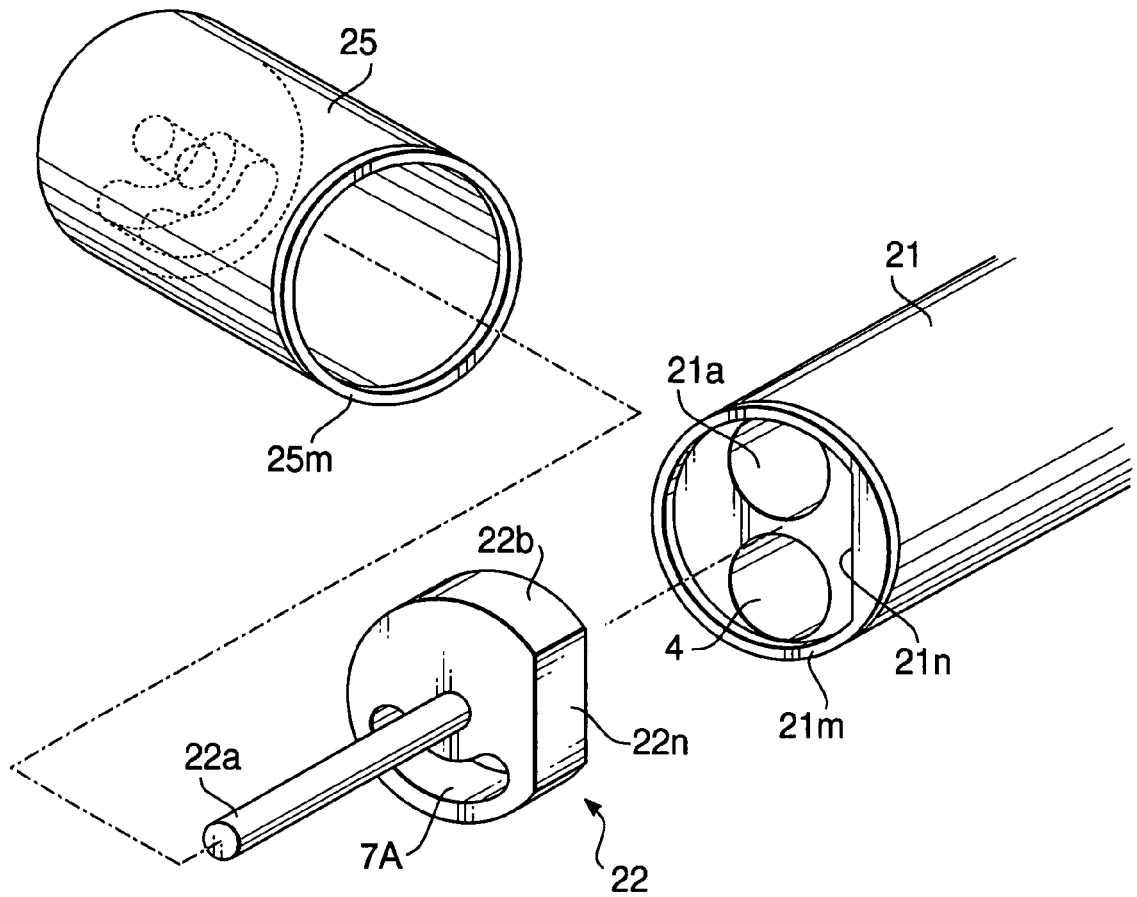
FIG. 9 is an exploded view of a tip portion of a high-frequency treatment tool according to a variation of the second embodiment of the invention.

With the above described configuration, a water hole 7A can be restricted from being moved to be in a misalignment with respect to the water channel 4. Further, as shown in FIG. 9, the magnetic member 21m of the sheath 21 and a base 22b of the electrode 22 may respectively be provided with linear portions 21n, 22n (locking system), which are adapted to fit with each other, so that the electrode 22 is not allowed to rotate inside the capping member 25.

The present disclosure relates to the subject matter contained in Japanese Patent Application No. 2005-032391, filed on Feb. 9, 2005, which is expressly incorporated herein by reference in its entirety.

What is claimed is:

1. A high-frequency treatment tool for an endoscope, comprising:
   a flexible sheath being made of electrically insulating material to be inserted through an insertion channel of the endoscope,
   a conductive operation wire, which is adapted to be advanced and retracted inside the flexible sheath; and
   a partially elongated electrode being arranged at a distal end of the high-frequency treatment tool separately from, and not structurally connected to, the operation wire, to which high-frequency electrical current is supplied for high-frequency treatment,
   wherein the electrode is adapted to be protruded and retracted in an axial direction thereof from the distal end of the high-frequency treatment tool by an operation to the operation wire, and
   wherein the electrode is allowed to be removed from the high-frequency treatment tool independently from the operation wire.

2. The high-frequency treatment tool according to claim 1, wherein the electrode is adapted to be advanced toward a distal end thereof by the operation wire.

3. The high-frequency treatment tool according to claim 2, further comprising a spring to provide expanding force toward a proximal end of the electrode to the electrode.

4. The high-frequency treatment tool according to claim 3, further comprising:
   an operation unit, which is provided at a proximal end of the flexible sheath and is adapted to advance and retract the operation wire, and
   a fixing member, which is provided to the operation unit to fix the operation wire in an arbitrary position with an arbitrary length of the electrode being protruded from the distal end of the high-frequency treatment tool.

5. The high-frequency treatment tool according to claim 1, further comprising:
   a capping member, which is detachably attached to the distal end of the flexible sheath, the capping member having an opening in which the electrode is adapted to traverse,
   wherein the electrode is allowed to be removed from the high-frequency treatment tool when the capping member is removed from the distal end of the flexible sheath.

6. The high-frequency treatment tool according to claim 5, wherein the capping member is adapted to be screwed to the distal end of the flexible sheath.

7. The high-frequency treatment tool according to claim 5, wherein the capping member is adapted to be attached to the distal end of the flexible sheath with magnetic intensity.

8. The high-frequency treatment tool according to claim 5, wherein the electrode includes a rod portion, which is formed to traverse inside the opening and to be protruded from the capping member, and a base portion, which is formed to loosely fit into an inner surface of the capping member, and
   wherein a spring is arranged compressedly inside the capping member.

9. The high-frequency treatment tool according to claim 8, wherein the operation wire is adapted to be in contact with a proximal surface of the base portion of the electrode.

10. The high-frequency treatment tool according to claim 9,
wherein a distal end of the operation wire includes a bent portion, which is formed to be bent sidewardly with respect to an axial direction of the operation wire, and
wherein the bent portion is adapted to be in contact with the proximal surface of the base portion of the electrode.

11. The high-frequency treatment tool according to claim 8,
wherein the sheath is therein provided with a water channel, which is arranged in parallel with the operation wire, and
wherein the base portion of the electrode and the capping member are respectively provided with a water hole, which is in an approximate straight alignment with respect to the water channel.

12. The high-frequency treatment tool according to claim 11, wherein the base portion of the electrode is provided with a locking system that is adapted to restrict the electrode from being rotated circumferentially with respect to the sheath.

13. An electrode for high-frequency treatment tool which is arranged separately from, and not structurally connected to, a conductive operation wire of the high-frequency treatment tool at a distal end of the high-frequency treatment tool, comprising:
a rod portion, which is formed to traverse inside an opening of a capping member of the high-frequency treatment tool and to be protruded from the capping member, and
a base portion, which is formed to loosely fit into an inner surface of the capping member,
wherein high-frequency electrical current is supplied for high-frequency treatment,
wherein the electrode is adapted to be protruded and retracted in an axial direction thereof from the distal end of the high-frequency treatment tool by an operation to the operation wire, and
wherein the electrode is allowed to be removed from the high-frequency treatment tool independently from the operation wire.

14. An endoscope with a high-frequency treatment tool for high-frequency treatment,
wherein the high-frequency treatment tool includes a flexible sheath being made of electrically insulating material to be inserted through an insertion channel of the endoscope, a conductive operation wire, which is adapted to be advanced and retracted inside the flexible sheath, and a partially elongated electrode being arranged at a distal end of the high-frequency treatment tool separately from, and not structurally connected to, the operation wire, to which high-frequency electrical current is supplied for high-frequency treatment,
wherein the electrode is adapted to be protruded and retracted in an axial direction thereof from the distal end of the high-frequency treatment tool by an operation to the operation wire, and
wherein the electrode is allowed to be removed from the high-frequency treatment tool independently from the operation wire.

* * * * *